(12) United States Patent
Lampropoulos et al.

(10) Patent No.: US 9,144,462 B2
(45) Date of Patent: Sep. 29, 2015

(54) INTRODUCER SHEATH AND HUB ASSEMBLY

(75) Inventors: Fred P. Lampropoulos, Salt Lake City, UT (US); Jim Mottola, South Jordan, UT (US); Arlin Dale Nelson, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 2242 days.

(21) Appl. No.: 11/669,009

(22) Filed: Jan. 30, 2007

(65) Prior Publication Data
US 2008/0183163 A1 Jul. 31, 2008

(51) Int. Cl.
*A61M 5/00* (2006.01)
*A61B 18/24* (2006.01)
*A61M 25/00* (2006.01)
*A61M 25/06* (2006.01)
*A61B 17/00* (2006.01)
*A61B 17/34* (2006.01)

(52) U.S. Cl.
CPC ............ *A61B 18/24* (2013.01); *A61M 25/0097* (2013.01); *A61M 25/0662* (2013.01); *A61B 17/00008* (2013.01); *A61B 17/3415* (2013.01); *A61B 2017/00469* (2013.01); *A61B 2017/347* (2013.01); *A61M 25/0631* (2013.01)

(58) Field of Classification Search
CPC ........... A61B 18/1492; A61B 17/3462; A61B 2018/00011; A61B 5/0084
USPC ................ 606/15, 7, 13, 16; 604/19–21, 177; 607/88, 89
See application file for complete search history.

(56) References Cited

U.S. PATENT DOCUMENTS

| | | | |
|---|---|---|---|
| 6,027,497 A * | 2/2000 | Daniel et al. .................... 606/15 |
| 6,126,654 A * | 10/2000 | Giba et al. ....................... 606/15 |
| 6,287,280 B1 * | 9/2001 | Lampropoulos et al. ................. 604/167.03 |
| 6,398,777 B1 | 6/2002 | Navarro et al. |
| 6,537,254 B1 * | 3/2003 | Schock et al. ................. 604/171 |
| 2004/0116912 A1 | 6/2004 | Appling |
| 2004/0153123 A1 * | 8/2004 | Palermo et al. ............... 606/213 |
| 2004/0199151 A1 | 10/2004 | Neuberger |
| 2005/0261630 A1 * | 11/2005 | Mottola et al. ........... 604/167.04 |
| 2006/0142747 A1 | 6/2006 | Appling |
| 2006/0217692 A1 | 9/2006 | Neuberger |
| 2008/0167542 A1 | 7/2008 | Lampropoulos et al. |

FOREIGN PATENT DOCUMENTS

WO WO 2004/089462 10/2004
WO WO 2006/052558 5/2006

OTHER PUBLICATIONS

O'Reilly et al., "Transcatheter Fiberoptic Laser Coagulation of Blood Vessels," vol. 142, No. 3, Mar. 1992, pp. 777-780.

* cited by examiner

*Primary Examiner* — Aaron Roane
(74) *Attorney, Agent, or Firm* — Stoel Rives LLP

(57) ABSTRACT

The present invention relates to medical treatment devices. In particular, according to one embodiment, the present invention a medical treatment device that includes, for example, a tube member, a treatment member by way of which energy can be transmitted in connection with performance of a medical procedure, a sleeve, and a hub member. In this example, the treatment member is positioned within the tube member and the tube member thus affords a degree or protection to the treatment member. The combination of the treatment member and the tube member is configured to be partially received within, and secured by, the hub member. In particular, the hub member includes a securement portion and a delivery portion which are releasably attached to each other.

19 Claims, 6 Drawing Sheets

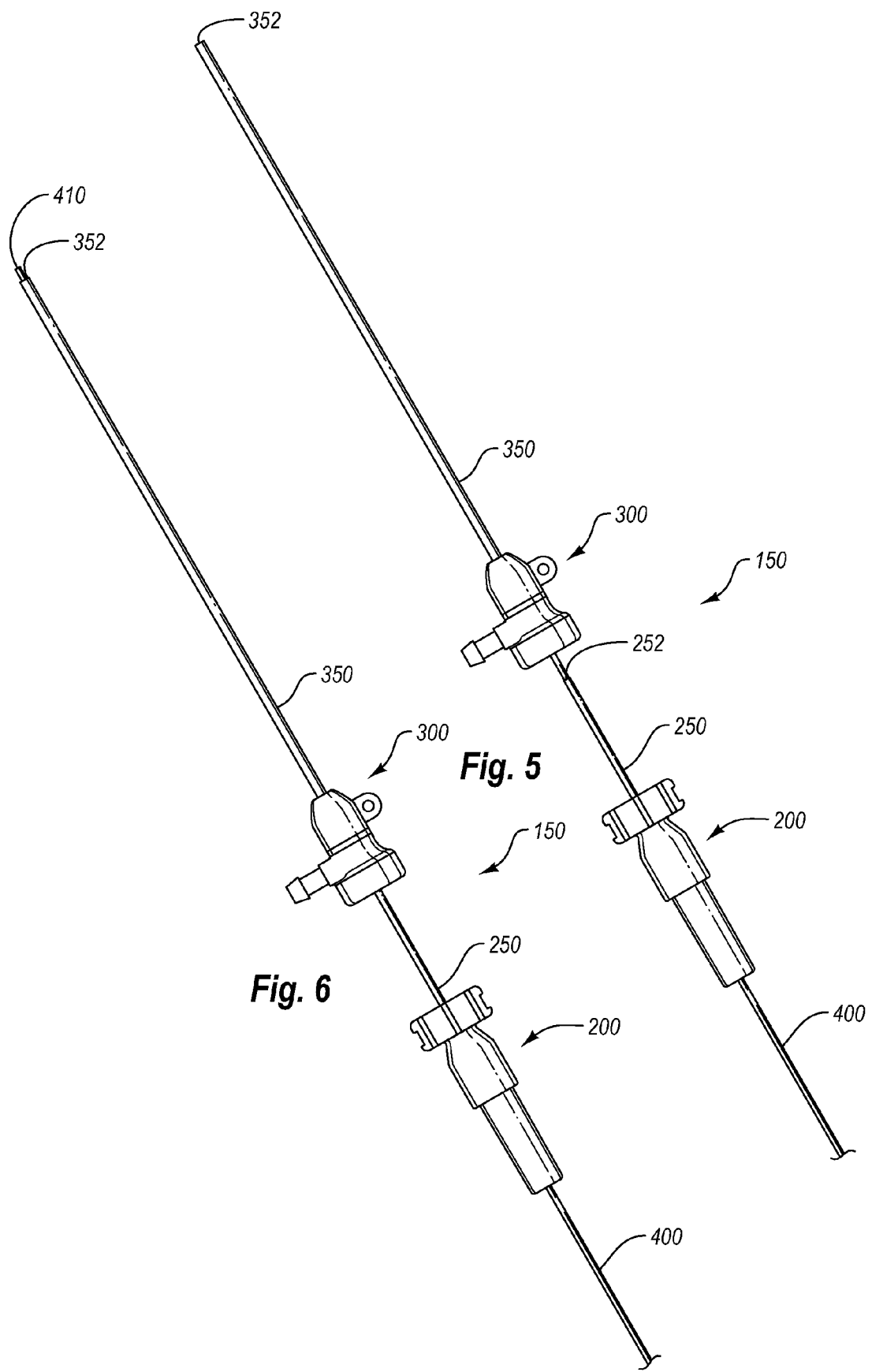

INTRODUCER SHEATH AND HUB ASSEMBLY

BACKGROUND OF THE INVENTION

The present invention relates to medical treatment devices. In particular, the present invention relates to an introducer sheath and hub for use with medical treatment devices that emit energy in connection with the performance of medical procedures. The present invention also relates to an introducer sheath and hub that may be used with other devices, such as those used in medical procedures.

One such medical device using energy is for vein ablation. Vein ablation is a procedure that may be used to treat varicose veins. Varicose veins exist because valves in the blood veins fail, allowing blood to stagnate. This stagnation causes pain and noticeable purple or red traces of the vein visible from the outside of the skin. During a normal vein ablation procedure for varicose veins, a practitioner first identifies a vein or veins for the procedure. The veins are then mapped as a guide for the practitioner in order for him to perform the procedure. Once the veins are mapped, the practitioner prepares the vein for ablation by introducing a sheath into a far end of the vein, in preparation for introduction of a treatment device, such as a laser or radio frequency device.

The treatment device is introduced into the vein at the distal end and extended in the vein to a junction with a healthy branch of a larger vein to ensure that the entire damaged vein is treated. In a laser treatment procedure, a fiber-optic member is covered by a sheath for introduction and for the treatment procedure. As fiber-optic members are usually very slender fibers of glass, it is not desirable to introduce the fiber-optic member without a covering because the fiber can break off in the patient, or can puncture the vein walls, damaging surrounding tissues.

Thus, the fiber-optic member is introduced in a sheath or catheter and advanced to the beginning of the treatment area. The practitioner can determine the location of the tip of the fiber-optic member in the patient by ultrasound imaging, transillumination of the anatomy using an aiming or targeting beam, by feel, and/or by estimating the location based on a calculated position inside of the vein targeted for treatment. Once the fiber-optic member reaches the beginning of the treatment area, the practitioner exposes a terminal portion of the fiber-optic member by extending the fiber-optic member out of the end of the sheath, exposing about 2 cm of fiber. To expose the end of the fiber, a practitioner looks at marks positioned on the fiber near a hub, indicating to the practitioner a position where the end of the fiber is inside of the sheath, and where the fiber is extended out of the sheath about 2 cm. The laser is then activated and transmits energy through the fiber, thereby heating the tissue and fluid around the end of the treatment fiber, effectively destroying the vein and preventing further filling of the vein with stagnant blood. The ablation procedure removes the appearance of the varicose vein, alleviates the pain caused by the varicose vein, and prevents further complications.

Additionally, in a traditional ablation procedure, a practitioner needs to monitor the energy expended by the laser to ensure sufficient treatment of the target veins. One way to see where the end of the treatment catheter is located inside of the patient is by seeing light through the patient's skin before or during the laser treatment of the target area. Light in the visible spectrum, which may be a targeting light, may be used. Thus, practitioners often dim the lights, allowing better viewing of the monitors and of the treatment location in the patient. However, the low-light conditions make seeing the marks on the fiber difficult, creating the possibility of errors because of misreading the marks. Thus, in placing a fiber for treatment into a patient in a traditional ablation procedure, a practitioner needs to identify markings on the fiber in very low light, simultaneously monitoring treatment, location of treatment, and patient comfort.

Some previous efforts to solve some of the problems associated with vein ablation procedures include, for example, a device and method disclosed in U.S. Patent Publication No. US 2006/0142747. In the disclosed device, a split straw is used to maintain a fiber inside of a sheath during insertion and prior to using the laser. The split straw includes a portion over the fiber, preventing the fiber from advancing in the sheath past a point where the terminal end of the fiber would be exposed outside of the sheath. The split straw also includes a second handle portion to aid in removing the split straw from the fiber, allowing a terminal end of the fiber to be advanced outside of the sheath.

However, the split straw can easily disconnect from the fiber during manipulation, such as during insertion of the sheath into the patient. For example, the handle portion can easily catch on other objects, removing the split sheath, or by pushing the fiber and sheath together, the angle of the split straw can cause the split straw to pop off of the fiber. If the split straw comes off prematurely, the split straw may become unusable by touching a non-sterile surface. Additionally, having the small split straw become disengaged from the fiber would cause problems for the practitioner in positioning the fiber correctly and completing the procedure.

Thus what is needed is a device that aids the practitioner by providing a fiber positioning system that is easy to use in low-light conditions and that can be employed without requiring the used of a removable piece that is easily lost or tends to premature deployment.

BRIEF SUMMARY OF AN EMBODIMENT OF THE INVENTION

The present invention relates to medical treatment devices. In particular, according to one embodiment, the present invention a medical treatment device that includes, for example, a tube member, a treatment member by way of which energy can be transmitted in connection with performance of a medical procedure, a sleeve, and a hub member. In this example, the treatment member is positioned within the tube member and the tube member thus affords a degree of protection to the treatment member. The combination of the treatment member and the tube member is configured to be partially received within, and secured by, the hub member. In particular, the hub member includes a securement portion, which may be used to secure the treatment member to the hub member, and a delivery portion, for use in delivering treatment to an individual. The securement portion and the delivery portion may be releasably attached to each other.

The securement portion may include a compression fitting that selectively secures and releases the treatment member. The securement portion may also be permanently affixed to the treatment member. Similarly, the sleeve member may be releasably coupled or permanently affixed to the treatment member, such that the sleeve member covers a portion of the treatment member.

The tube member may be permanently coupled to the delivery portion. In some embodiments, the tube member may be placed inside of an individual during a medical procedure, such as during a laser vein ablation procedure, with a fiber-optic member as the treatment member.

The delivery portion may also include a side port configured to allow passage of fluids between the side port and a distal end of the tube member. The delivery portion may also include a seal configured to reduce passage of fluids from the delivery portion to the securement portion. The delivery portion and the securement portion may be removably coupled with a snap or pressure fit such that the securement portion and delivery portion each include complementary features, such that a complementary feature of one of the securement or delivery portion deforms to fit into the complementary feature of the other portion.

In some embodiments, the sleeve member may have a length of between 1 and 3 cm, and may cover a portion of the treatment member. The treatment member may be configured to slide into the tube member through the delivery portion. The sleeve member may also be configured to slide into the delivery portion along with the treatment member. With the treatment member partially inserted into the delivery portion and the tube member, the sleeve member may releasably hold the securement portion apart from the delivery portion by resisting entry of the sleeve member into the delivery portion by requiring deformation by the seal for entry of the sleeve member into the delivery portion. The sleeve member may be permanently affixed to the securement portion.

The delivery portion and the securement portion may be removably coupled together with a snap or pressure fit, such that the securement portion and delivery portion each include complementary features, wherein one of the complementary features deforms to fit into the other complementary feature.

Some embodiments may include a kit containing a dilator, a guide wire, a treatment member, a hub, a tube member coupled to a portion of the hub, and a sleeve member permanently coupled to a different portion of the hub.

These and other aspects of the present invention will become more fully apparent from the following description and appended claims.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. The invention will be described and explained with additional specificity and detail through the use of the accompanying drawings in which:

FIG. 5 is a perspective view of the assembly of FIG. 1;

FIG. 6 is a perspective view of the assembly of FIG. 1 in a configuration ready for placement.

DETAILED DESCRIPTION OF EXEMPLARY EMBODIMENTS

In the illustrated embodiments, aspects of an introducer sheath assembly are disclosed and described below.

Figure 1:
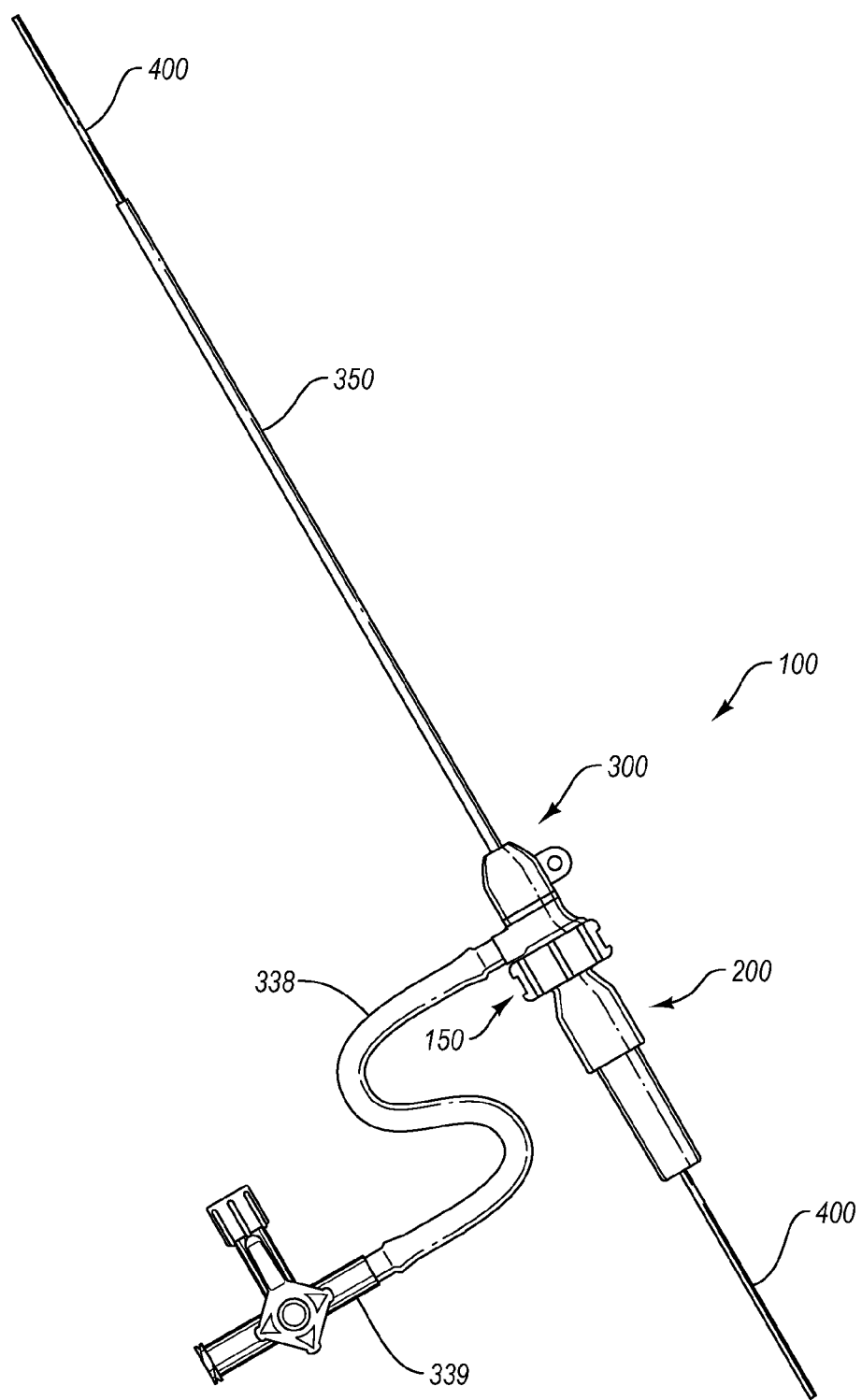
FIG. 1 is a perspective view of an example embodiment of an introducer sheath and hub assembly.

FIGS. 1-7 illustrate device 100, including hub 150, introducer sheath 350, and treatment member 400. Hub 150 includes securement portion 200 and delivery portion 300. FIG. 1 illustrates hub 150 in an assembled state, with securement portion 200 coupled with delivery portion 300. Treatment member 400 traverses hub 150, passing through securement portion 200 and delivery portion 300, and extending from a distal end of introducer sheath 350. Delivery portion 300 is coupled to tube 338. Tube 338 is coupled to stopcock 339 which may be used to evacuate or provide fluids or materials through introducer sheath 350.

Treatment member 400 may be a fiber-optic member, an electrical conductor, or other suitable material configured to convey energy to a treatment site. Some energy sources that may be used with treatment member 400 may include RF, microwave, ultrasound, heated fluid, radiant light, lasers, electrical conduction, or other energy sources used in medical procedures.

Figure 2:
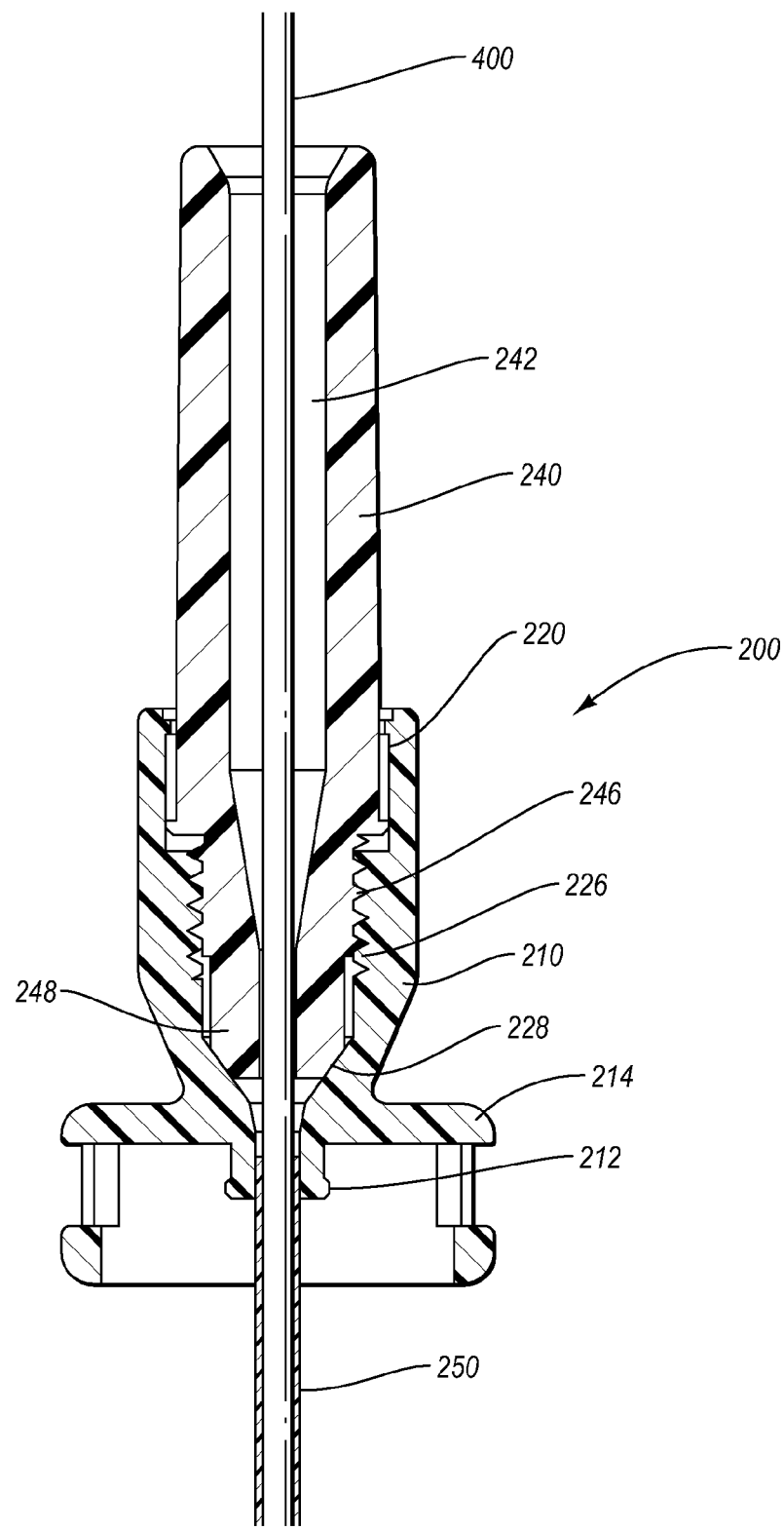
FIG. 2 is a cross-sectional view of a portion of the assembly of FIG. 1.
Figure 3:
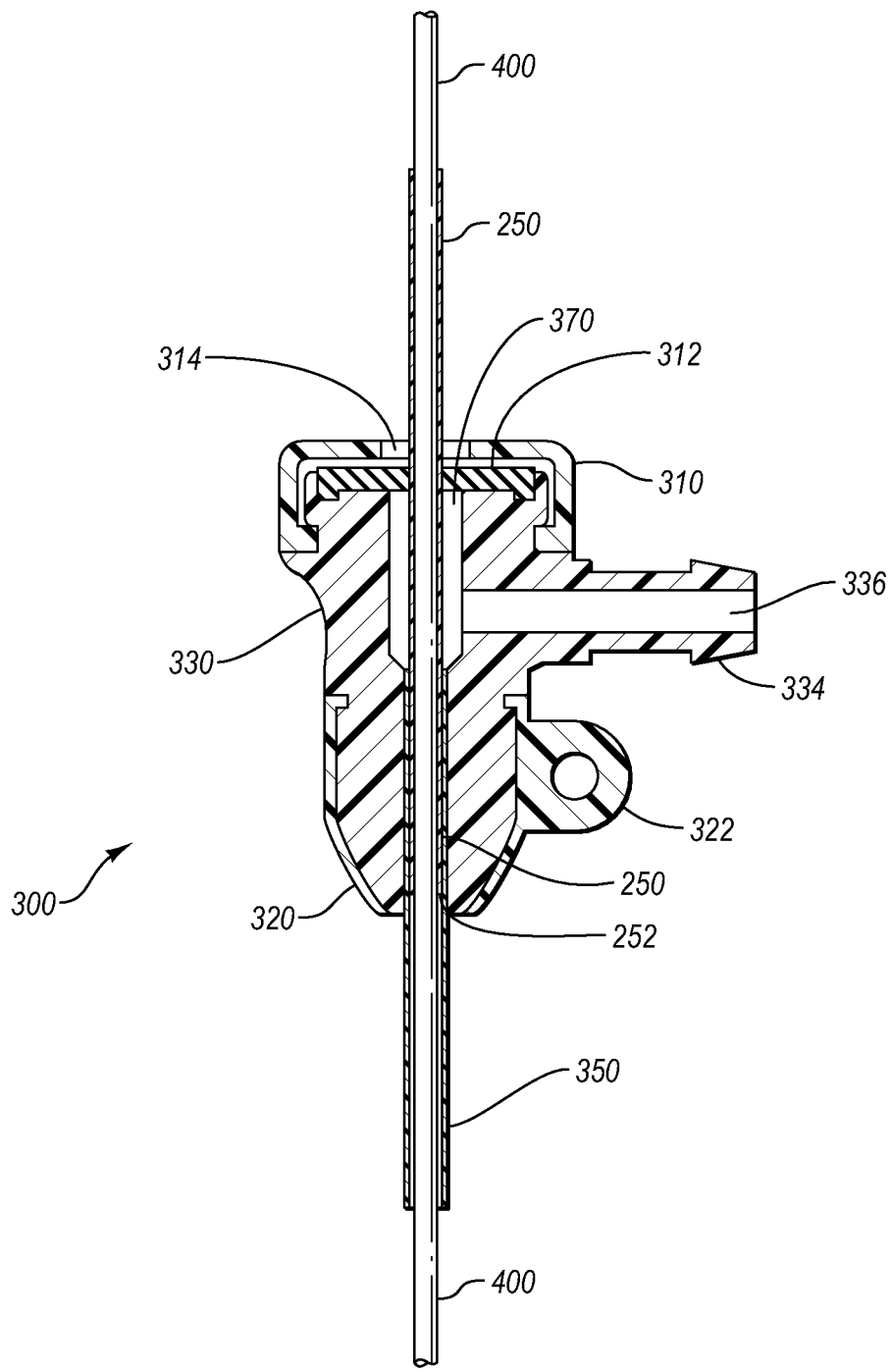
FIG. 3 is a cross-sectional view of a portion of the assembly of FIG. 1.

FIGS. 2 and 3 illustrate cross-sectional views of securement portion 200 and delivery portion 300, respectively. Securement portion 200 may be configured to hold treatment member 400 in a fixed position, allowing manipulation of treatment member 400. For example, in a vein ablation procedure, securement portion 200 may be used to manipulate treatment member 400 through delivery portion 300 and into introducer sheath 350 in preparation for a vein ablation procedure. Similarly, securement portion 200 may be coupled to sleeve member 250, which may be configured to provide a guide to how far treatment member 400 is inserted into introducer sheath, as described below with particularity in connection with FIGS. 5 and 6. In FIG. 2, securement portion 200 includes collar 210 and barrel 240. Collar 210 includes tabs 212, flange 214, collar passageway 220, collar threads 226, and engagement surface 228. Barrel 240 includes barrel passageway 242, barrel threads 246, and compression tabs 248. Barrel 240 may be releasably coupled to collar 210 by engaging barrel and collar threads 246, 226, respectively, which cooperate to hold collar 210 and barrel 240 together.

Treatment member 400 is shown in FIG. 2 as passing through collar passageway 220 and barrel passageway 242. When treatment member 400 is located in barrel passageway 242, securement portion 200 may hold treatment member 400 by way of tightening of the threaded connection of collar 210 and barrel 240. The threaded connection may be a conventional threaded interface such that by turning barrel 240 with respect to collar 210, barrel 240 and collar 210 are coupled together or uncoupled, depending on the turning direction.

In some embodiments, when coupling collar 210 and barrel 240, engagement surface 228 presses against compression tabs 248, causing compression tabs 248 to move inwardly, toward the center of barrel 240, constricting barrel passageway 242. In such embodiments, when treatment member is 400 is located in barrel passageway 242, this constriction causes compression tabs 248 to press against and frictionally hold treatment member 400 axially with respect to securement portion 200. Selective loosening and tightening of securement portion 200 can enable adjustment of a length of treatment member 400 extending from securement member 200. For example, in a vein ablation procedure, the length of treatment member extending from securement member 400 will correlate to the length of introducer sheath 350 (FIGS. 3-6) and sleeve member 250, as described in more detail below.

In other embodiments, other ways of holding treatment member 400 with securement portion 200 may be employed. For example, securement portion 200 may include a lever that causes a compression hold with treatment member 400, or treatment member 400 may be permanently affixed to securement portion 200 by adhesives, welding, monolithic construction, or any other way of securing treatment member 400 with securement portion 200.

As shown in FIG. 2, securement portion 200 also includes tabs 212. Tabs 212 may function with corresponding features of delivery portion 300 to removably couple securement portion 200 and delivery portion 300 together, as described in more detail below with regard to FIG. 4. Tabs 212 may also hold sleeve member 250. Sleeve member 250 may be permanently affixed, by adhesives, welding, or other suitable attachment, or may be selectively removable from securement member 200. As shown in FIG. 2, sleeve member 250 may be of tubular construction and sized such that treatment member 400 passes through sleeve member 250. The diameter of sleeve member 250 may be such that the inner diameter of sleeve member 250 is slightly larger than the outer diameter of treatment member 400, such that a close fit between sleeve member 250 and treatment member 400 is achieved.

The length of sleeve member 250 may correlate with a desired exposed at treatment length of distal end 410 of treatment member 400. In a vein ablation procedure, treatment lengths may range from about 1-4 cm. Thus, sleeve member 250 may be from about 1-4 cm long, or any other length as desired by the practitioner. One particular use of device 100 with sleeve member 250 is described in further detail below.

As shown in the exemplary embodiment of FIG. 3, delivery portion 300 of device 100 includes cap 310, body 330, and cover 320. As illustrated, cap 310 includes top opening 314 which may be located in the center of cap 310 and positioned such that opening 314 is part of channel 370 when cap 310 is located over body 330. Cap 310 may also function to hold seal 312 in place between body 330 and cap 310. Cap 310 may be permanently affixed or removably coupled to body 330. In some embodiments, cap 310 may be integrally formed with body 330.

Seal 312 may be arranged to prevent materials, such as blood and fluids, from exiting channel 370 through opening 314 while allowing introduction of tools, instruments, and other devices, such as treatment member 400 and sleeve member 250, through opening 314. Seal 312 may be made from a pliable material such as rubber, plastic, or other suitable material. Seal 312 may have a slit or a plurality of slits such that seal 312 may be penetrated by an introduced object, such as treatment member 400 or sleeve member 250, but retain a substantially closed configuration when not being penetrated. Seal 312 may also continue to form a seal around an introduced object, allowing the introduced object to slidably move along channel 370 while maintaining a seal preventing materials from exiting channel 370 around an introduced object.

Body 330 includes port 334 and side-channel 336 passing through port 334 to allow introduction or removal of materials from a distal end of introducer sheath 350 through channel 370. For example, a vacuum may be applied to side-channel 336 through tube 338 and stopcock 339 (shown in FIGS. 1, 7) to evacuate blood or other fluids during a medical procedure. Tube 338 may be attached to port 334, and may be held to port 334 by features configured to aid in the retention of tube 338 to port 334.

Similarly, body 330 may be permanently affixed or removably coupled to introducer sheath 350 such that movement of delivery portion 300 may also move introducer sheath 350. For example, during a vein ablation procedure, introducer sheath 350, treatment member 400, and hub 350 may be simultaneously withdrawn.

Cover 320 may be rotatably coupled to body 330. Cover 320 may include portion 322, which may be used to secure device 100 in a particular location, for example by tape or suture, while allowing rotational movement of body 330 and, by extension, all other portions of device 100, within cover 320, allowing a practitioner to rotate introducer sheath, treatment member 400, or other portion as required by a particular procedure.

Figure 4:
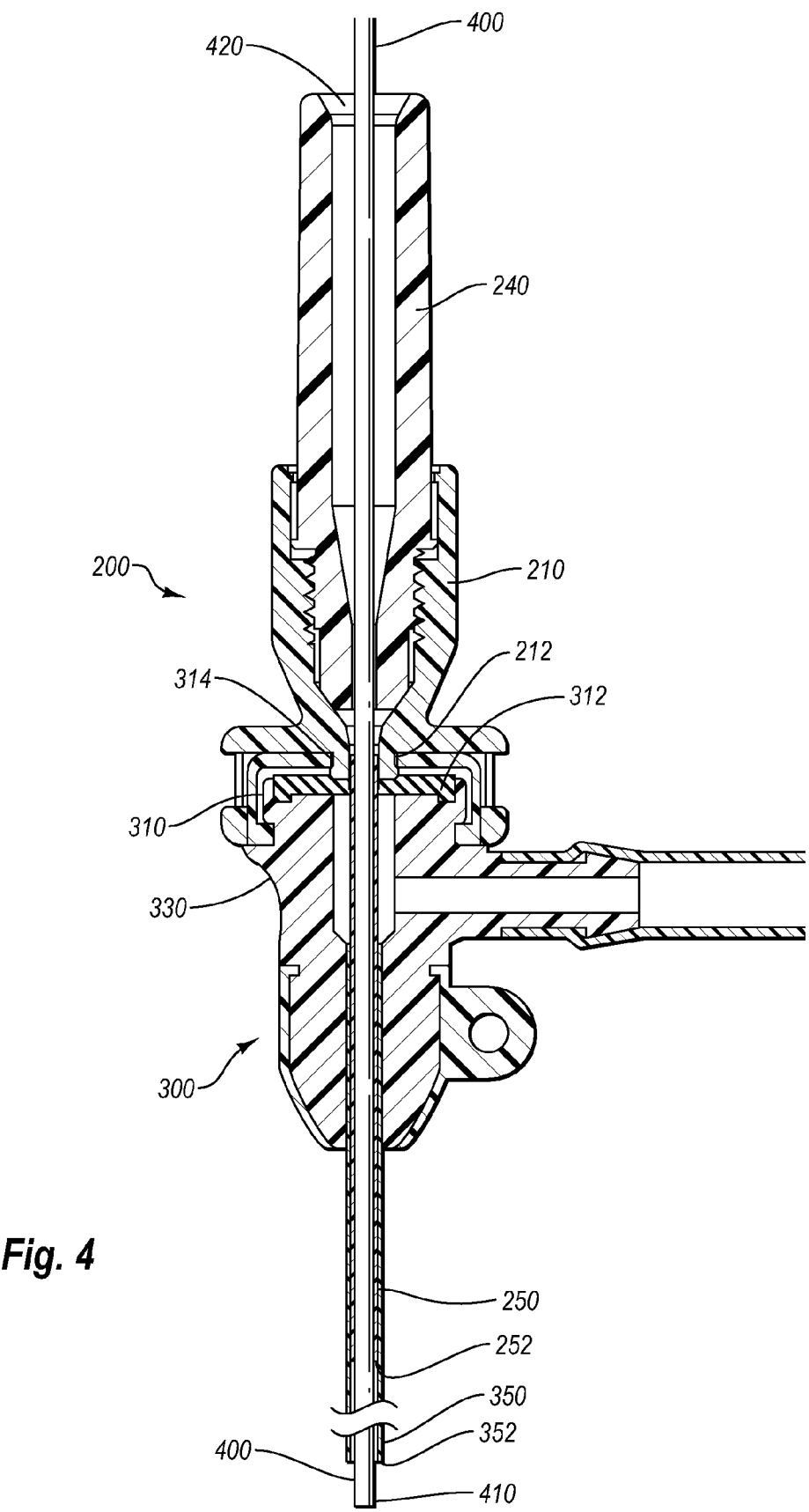
FIG. 4 is a cross sectional view of a portion of the assembly of FIG. 1.

FIG. 4 shows a cross-sectional view of securement portion 200 and delivery portion 300 in a coupled configuration. FIGS. 5 and 6 show sequential steps that may be used to couple securement portion 200 and delivery portion 300 for use in a medical procedure such as vein ablation. In a vein ablation procedure, a practitioner may want to insert distal end 410 of treatment member 400 into a patient to access a treatment area. A practitioner may create an initial opening into the patient and the desired vein by using conventional procedures such as by using a trocar. Once an opening is created, a dilator and/or guide wire may be used to create the desired pathway into the vein targeted for treatment.

Prior to use in a vein ablation procedure, device 100 may be prepared for use in the procedure. To prepare device 100 for use in the procedure, treatment member 400 may be secured to securement portion 200. The location of securement portion 200 on treatment member 400 may be predetermined such that the length of treatment member extending between distal end 410 of treatment member 400 and securement portion 200 is about the same length as introducer sheath 350 plus about 1-4 cm, which corresponds to the length of sheath member 250.

Distal end 410 of treatment member 400 may then be inserted into channel 370 of delivery portion 300 through seal 312, (shown in FIGS. 4-5), and advanced until distal end 252 of sleeve member 250 contacts seal 312, as shown in FIG. 6. Because the diameter of sleeve member 250 is larger than the diameter of treatment member 400, a practitioner may feel resistance as distal end 252 of sleeve member 250 contacts seal 312. In this configuration, distal end 410 of treatment member 400 may be located at distal end 352 of introducer sheath 350, such that distal end 410 of treatment member 400 may be somewhat inside, even with, or somewhat extending from distal end 352 of introducer sheath 350, as desired by the practitioner.

With distal end 410 of treatment member 400 positioned about at distal end 352 of introducer sheath 350, distal end 410 of treatment member 400 may be protected by introducer sheath 350 from being damaged and from damaging tissues when being placed in a desired location in a patient.

Figure 7:
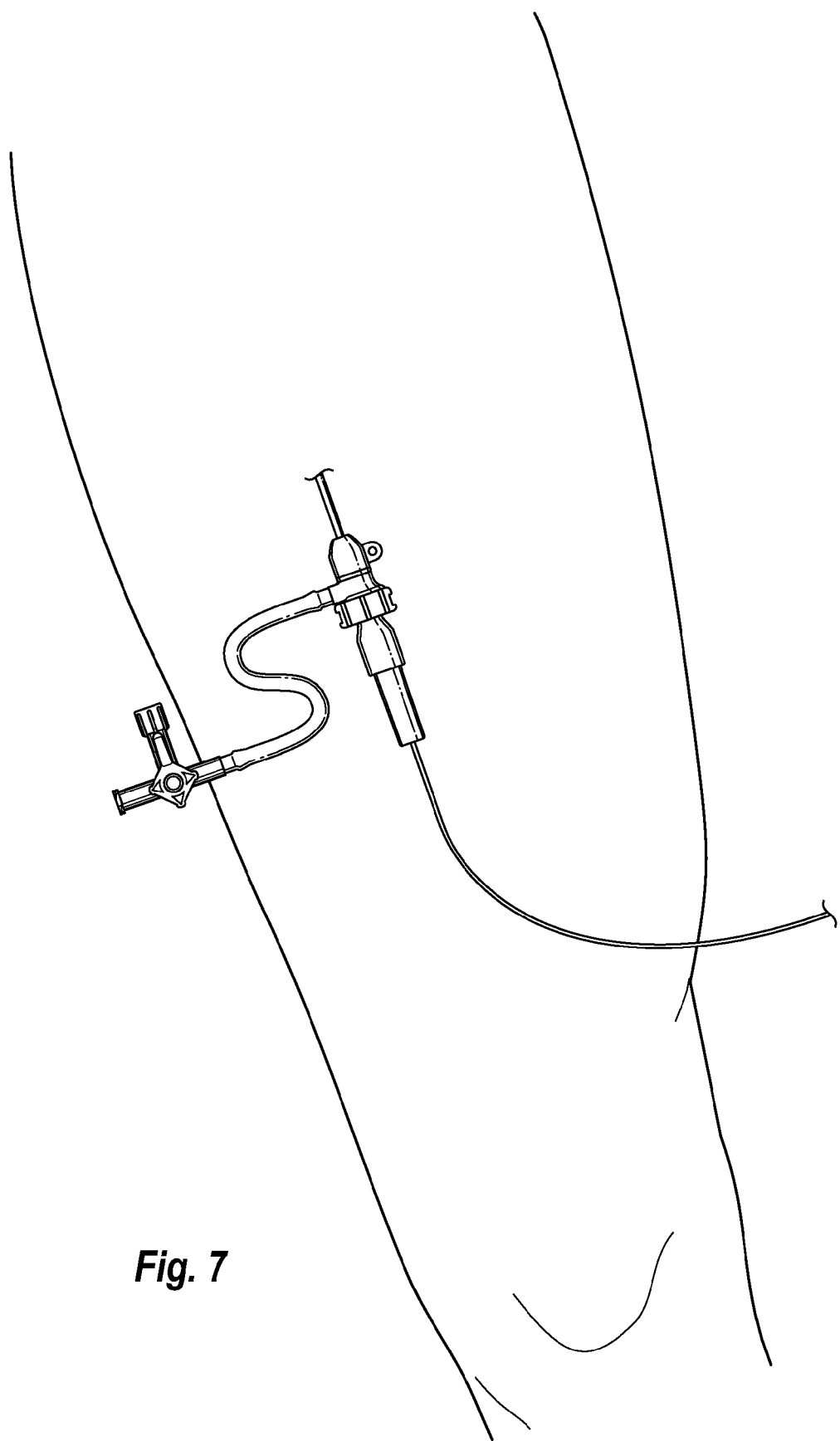
FIG. 7 is a perspective view of the assembly in a placed configuration.

In a vein ablation procedure, for example, once the pathway into the targeted vein is established, and device 100 prepared for use in the procedure, introducer sheath 350 and treatment member 400 may be introduced into the patient. Introducer sheath 350 may be used to assist in placing treatment member 400 in the desired location in a patient, as shown in FIG. 7. Once the desired location is reached, a practitioner may then push sleeve member 250 through seal 312 until tabs 212 push through opening 314 of cap 310, thereby coupling securement portion 200 to delivery portion 300, as shown in FIG. 4.

In the coupled position, as shown in FIG. 4, distal end 410 of treatment member 400 may extend from distal end 352 of introducer sheath 350 a distance that is about the same as the length of the sleeve member 250, assuring the practitioner that the device 100 is properly positioned and ready for use. If the practitioner determines that more or less of distal end 410 of treatment member 400 should be exposed, securement portion 200 may be loosened and repositioned on treatment member 400, as described above, for adjustmenting the positioning of distal end 410 with respect to distal end 352 of introducer sheath 350. Such adjustments may be made at any time before or during a procedure, as desired by a practitioner.

In some embodiments, sleeve member 250 may be color coded such that a particular color corresponds to a particular length. In other embodiments, sleeve member 250 may be cut to a desired length by a practitioner, or several different sleeve members 250 having distinct lengths may be provided.

In some embodiments, device 100 may be packaged in a kit, which may include items that may be used in conjunction with device 100. For example, a kit may include a trocar, a dilator, a guide wire, at least one introducer sheath 350 coupled to delivery portion 300, and treatment member 400, having a length corresponding to the length of introducer sheath 350, coupled to securement portion 300. Thus, a practitioner may then prepare the patient using the supplementary items in the kit for use with device 100, and use device 100 as described above. In some embodiments, the kit may include a plurality of sleeve members 250 having different lengths.

Each portion of device 100 may be manufactured of materials suitable for use in medical procedures, and may be sterilized with an appropriate sterilization method. Although device 100 has been described above in conjunction with a vein ablation procedure, device 100 may also be used in other medical procedures and practices when such an assembly might be useful or desirable.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A device, comprising:
   a tube member;
   a treatment member, having a first diameter, disposed at least partly within the tube member and having a distal end configured to deliver energy in connection with performance of a medical procedure;
   a hub member, comprising:
      a securement portion configured to secure the hub member to the treatment member;
      a seal positioned between the tube member and the securement portion; and
      a delivery portion coupled to the tube member, wherein the securement portion and the delivery portion are configured to be removably coupled together; and
   a sleeve member having a second diameter; wherein the sleeve member is disposed about the treatment member; wherein the second diameter is larger than the first diameter, such that as the treatment member is advanced through the seal, the sleeve member contacts the seal and provides resistance to further advancement of the treatment member, and wherein the securement portion and the delivery portion are spaced apart from each other at a pre-determined distance such that, contact between a distal end of the sleeve member and the seal correlates to disposition of the treatment member with respect to the delivery portion in an advancement position wherein the delivery member protects the treatment member from damage and/or from damaging body tissue and
   disposition of the distal end of the sleeve distal of the seal correlates to disposition of the treatment member with respect to the delivery portion in a treatment position wherein the treatment member extends from the delivery member such that the treatment member may be used for treatment.

2. The device of claim 1, wherein the securement portion comprises a compression fitting configured to selectively secure and release the treatment member.

3. The device of claim 1, wherein the securement portion is permanently affixed to the treatment member.

4. The device of claim 1, wherein the treatment member is a fiber-optic.

5. The device of claim 4, wherein the energy is light energy associated with a laser.

6. The device of claim 1, wherein the delivery portion includes a port configured to allow passage of fluids between the side port and a distal end of the tube member.

7. The device of claim 1, wherein the tube member is permanently coupled to the delivery portion.

8. The device of claim 1, wherein the sleeve member is configured to slide into the delivery portion through the seal.

9. The device of claim 8, wherein the sleeve member is configured to maintain the securement portion and delivery portion is the spaced apart arrangement until the seal is sufficiently deformed to permit the sleeve member to penetrate the seal and enter the delivery portion.

10. The device of claim 1, wherein the sleeve member is permanently affixed to the securement portion.

11. The device of claim 1, wherein the sleeve member has a length between 1 and 3 cm.

12. The device of claim 1, wherein the delivery portion and the securement portion include respective complementary features, that enable the delivery portion and the securement portion to be releasably engaged with each other.

13. The device of claim 1, wherein a distal end of the treatment member is adjacent to a distal end of the delivery member when the sleeve contacts the seal.

14. A device, comprising:
   a treatment member;
   a hub member, including:
   a securement portion configured to secure the hub member to the treatment member; and
   a delivery portion, wherein the securement portion is directly coupled to the delivery portion; and
   a sleeve member coupled to the securement portion, wherein the sleeve member is configured to hold the securement portion and the delivery portion apart from each other at a pre-determined distance in a first arrangement wherein the treatment member is in an advancement position with respect to the delivery portion such that the delivery portion protects the treatment member from damage and/or from damaging body tissue, and configured to provide an indication of the relative position of the treatment member with respect to the delivery portion, and wherein the sleeve member is further configured to at least partially reside in the hub member in a second arrangement wherein the treatment member is in a treatment position with respect to the delivery portion such that the treatment member extends from the delivery portion such that the treatment member may be used for treatment.

15. The device of claim 14, further comprising a sheath within which the treatment member is at least partially disposed, wherein the sheath is coupled to the delivery portion, and wherein the sheath is configured to be used in a medical procedure.

16. The device of claim 15, wherein the sheath is configured to cover a distal end of the treatment member in the first arrangement, and wherein the pre-determined distance corresponds to a distance that the distal end of the treatment member extends from the distal end of the sheath in the second arrangement.

17. The device of claim 14, wherein the treatment member is an optical fiber.

18. The device of claim 1, wherein the device is configured such that when the sleeve contacts the seal, a distal end of the treatment member is adjacent to a distal end of the delivery member, and wherein the sleeve may be advanced through the seal a distance sufficient to deploy a portion of the treatment member sufficient to facilitate treatment.

19. The device of claim 18, wherein the treatment member is configured to extend from 1 to about 4 cm beyond the distal end of the delivery member.

\* \* \* \* \*

UNITED STATES PATENT AND TRADEMARK OFFICE
CERTIFICATE OF CORRECTION

| | | |
|---|---|---|
| PATENT NO. | : 9,144,462 B2 | |
| APPLICATION NO. | : 11/669009 | |
| DATED | : September 29, 2015 | |
| INVENTOR(S) | : Fred P. Lampropoulos, Jim Mottola and Arlin Dale Nelson | |

It is certified that error appears in the above-identified patent and that said Letters Patent is hereby corrected as shown below:

In the claims

Column 8, Line 30 reads ". . . portion is the spaced apart . . ." which should read ". . . portion in the spaced apart . . ."

Signed and Sealed this
Seventh Day of June, 2016

Michelle K. Lee
*Director of the United States Patent and Trademark Office*